United States Patent
Inoue et al.

(10) Patent No.: US 6,932,773 B2
(45) Date of Patent: Aug. 23, 2005

(54) WRIST TYPE BLOOD PRESSURE METER CUFF

(75) Inventors: Tomonori Inoue, Kyoto (JP); Osamu Shirasaki, Amagasaki (JP); Yoshihiko Sano, Kyoto (JP); Toshio Ohtani, Kyoto (JP)

(73) Assignee: Omron HealthCare Co., Ltd., Kyoto (JP)

( * ) Notice: Subject to any disclaimer, the term of this patent is extended or adjusted under 35 U.S.C. 154(b) by 0 days.

(21) Appl. No.: 10/755,685

(22) Filed: Jan. 13, 2004

(65) Prior Publication Data

US 2004/0193059 A1 Sep. 30, 2004

(30) Foreign Application Priority Data

Jan. 22, 2003  (JP) .......................................... 2003-013716

(51) Int. Cl.⁷ ................................................. A61B 5/02
(52) U.S. Cl. ...................... 600/499; 600/485; 600/490
(58) Field of Search ................................. 600/485–504

(56) References Cited

U.S. PATENT DOCUMENTS

| | | | | |
|---|---|---|---|---|
| 6,231,517 B1 | * | 5/2001 | Forstner ...................... | 600/485 |
| 6,336,901 B1 | * | 1/2002 | Itonaga et al. ............... | 600/499 |
| 6,514,212 B1 | * | 2/2003 | Ide et al. ..................... | 600/490 |
| 6,694,821 B2 | * | 2/2004 | Yamakoshi et al. ........... | 73/756 |
| 2004/0010198 A1 | * | 1/2004 | Yamakoshi et al. .......... | 600/499 |

FOREIGN PATENT DOCUMENTS

| | | |
|---|---|---|
| CH | 616801 | 11/1976 |
| DE | 100 28 596 | 6/2000 |
| EP | 1 074 216 | 2/2000 |
| EP | 1 369 080 | 5/2003 |
| JP | A 61-11019 | 1/1986 |
| JP | 11-318835 | 5/1998 |

OTHER PUBLICATIONS

European Search Report mailed May 3, 2004.

* cited by examiner

Primary Examiner—Robert L. Nasser
Assistant Examiner—Patricia Mallari
(74) Attorney, Agent, or Firm—Morrison & Foerster LLP (57) ABSTRACT

Provide is a wrist type blood pressure meter cuff not oppressing the non-selected artery so as to prevent its pulse waves from mixing into pulse waves of the selected artery necessary for measurement, in a cuff used in a blood pressure meter for measuring blood pressures by selecting and oppressing one artery of the wrist. A wrist type blood pressure meter cuff comprises a fluid bag for oppressing a selected artery of either radial artery or ulnar artery located at the wrist by feeding fluid inside to inflate, and a fixing member for fixing the fluid bag at the wrist. By forming a gap between the fixing member and the wrist, the oppressing pressure directly applied from the fixing member to the wrist at which the non-selected artery is located is set smaller than the oppressing pressure directly applied from the fixing member to other position of the wrist when oppressing the wrist by inflating the fluid bag. This gap is produced by a swollen part provided in the fixing member.

6 Claims, 7 Drawing Sheets

PRIOR ART

Fig. 9B

PRIOR ART

Fig. 9C

PRIOR ART

WRIST TYPE BLOOD PRESSURE METER CUFF

BACKGROUND OT THE INVENTION

1. Field of the Invention

The present invention relates to a wrist type blood pressure meter cuff comprising a fluid bag filled with fluid such as air for oppressing a selected artery of the wrist, and a fixing member for fixing the fluid bag to the wrist.

2. Description of the Prior Art

The wrist on which a wrist type blood pressure meter is worn includes two arteries, the radial artery and ulnar artery, and it is general to oppress both of them when measuring the blood pressures in the wrist type blood pressure meter. However, the radial artery and ulnar artery at the wrist are somewhat deeply seated between the two bones of radius and ulna and parallel tendons. In certain users, by the conventional cuff, the oppressing pressure of the fluid bag does not reach sufficiently to the arteries, and the arteries are not oppressed sufficiently, and accurate blood pressure measurements may not be obtained. As compared with the brachial artery which was traditionally measured because there is no tendon around one bone and it is relatively easy to oppress, the carpal arteries are deeply seated as mentioned above and are not easily reached by the oppressing pressure of the fluid bag.

Besides, a large oppressing pressure is needed for oppressing two arteries, and the user suffers a large oppressing pressure during measurement and it is not comfortable for the user.

To solve these problems, it has been proposed to oppress only one selected artery out of the two arteries running in the wrist and measure blood pressures (for example, see patent document 1). The cuff used in this method of blood pressure measurement has a shape suited to oppress its fluid bag only to one of the two arteries in the wrist, this fluid bag is fitted to the inside of a band as a fixing member.

The patent document 1 is JP-A 61-11019.

To oppress only one selected artery and measure blood pressures, it is required to detect pulse waves of the selected artery only. That is, pulse waves of other non-selected artery must be prevented from mixing into the desired pulse waves to be detected.

Figure 9A:
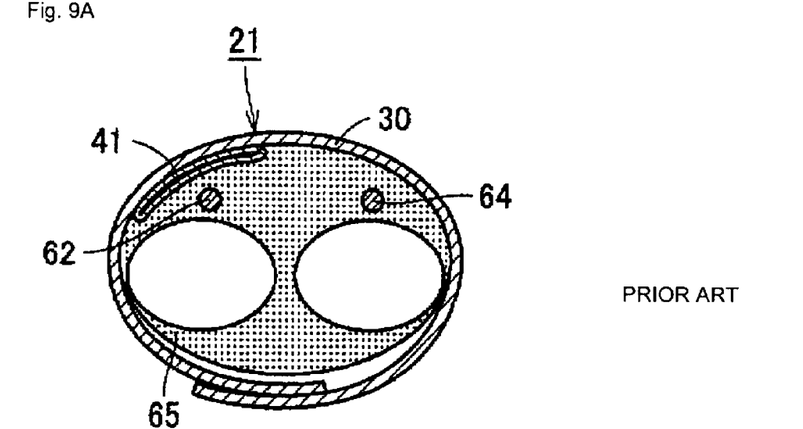
FIG. 9 shows a sectional view explaining the state of use of a wrist type blood pressure meter cuff in a prior art.
Figure 9B:
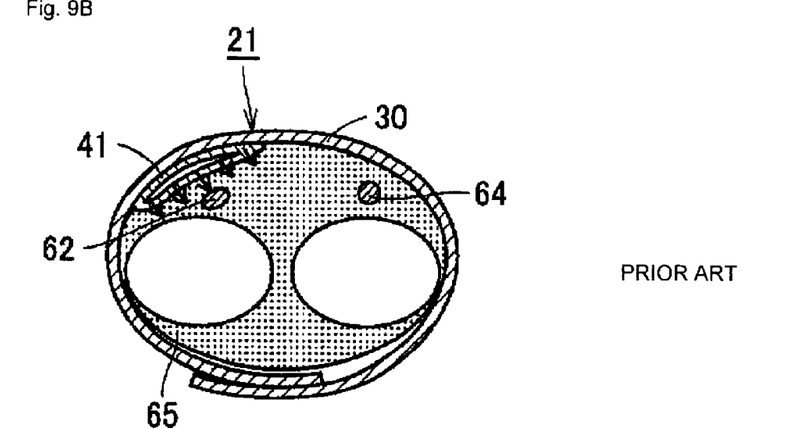
Figure 9C:
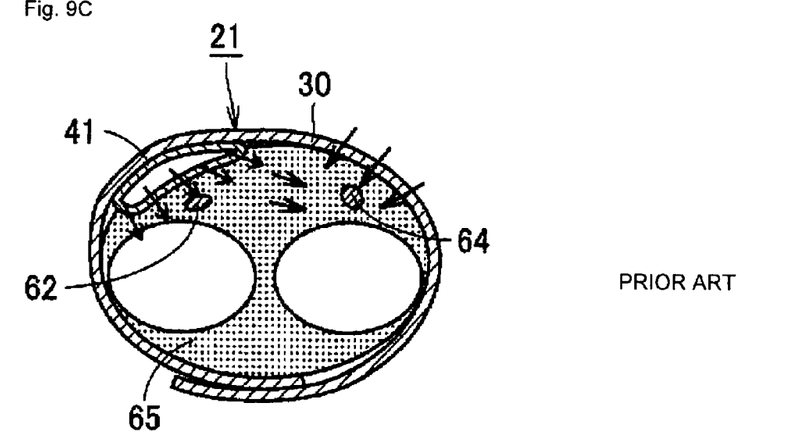

When the cuff is composed as described above, as shown in FIG. 9A, before a fluid bag 41 is inflated with air, pressure is applied to neither a selected artery 62 nor a non-selected artery 64. When air is charged in the fluid bag 41 and as the fluid bag 41 is inflated, the oppressing pressure of the fluid bag 41 is applied to the selected artery 62 (FIG. 9B). As the fluid bag 41 is further expanded, the gap between the fixing member 30 and outer periphery of the wrist 65 is eliminated, and the fixing member 30 applies a force to tighten the entire wrist 65 (FIG. 9C). As a result, the non-selected artery 64 is also oppressed by the fixing member 30, and pulsations of the non-selected artery are mixed with the pulsations of the selected artery 62 necessary for measurement, and measurement of blood pressures is disturbed.

SUMMARY OF THE INVENTION

The invention is devised to solve these problems, and it is hence an object thereof to present a wrist type blood pressure meter cuff not oppressing the non-selected artery so as to prevent its pulse waves from mixing into pulse waves of the selected artery necessary for measurement, in a cuff used in a blood pressure meter for measuring blood pressures by selecting and oppressing one artery of the wrist.

A wrist type blood pressure meter cuff of the invention comprises a fluid bag for oppressing a selected artery of either radial artery or ulnar artery located at the wrist by feeding fluid inside to inflate, and a fixing member for fixing the fluid bag at the wrist, in which the fixing member has a structure so that the oppressing pressure directly applied from the fixing member to the wrist at which the non-selected artery is located may be smaller than the oppressing pressure directly applied from the fixing member to other position of the wrist when oppressing the wrist by inflating the fluid bag.

According to this wrist type blood pressure meter cuff, since the oppressing pressure directly applied from the fixing member to the non-selected artery is smaller than the oppressing pressure directly applied from the fixing member to other position of the wrist, the oppressing force of the fixing member applied to the non-selected artery may be small. As a result, pulsations of the non-selected artery are hardly transmitted to the fluid bag connected a sensor or the like for detecting the pulsations of the selected artery. Hence, the pulse waves of the non-selected artery are prevented from mixing into pulse waves of the selected artery necessary for measurement of blood pressures, and disturbance of measurement of blood pressures can be avoided.

In the wrist type blood pressure meter cuff, preferably, the fixing member has a shape so as to form a gap at least in part of the wrist surface at which the non-selected artery is located, when the wrist type blood pressure meter cuff is fixed at the wrist in a contracted state of the fluid bag. In this configuration, at least in a contracted state of the fluid bag, a gap is formed between the wrist surface at which the non-selected artery is located and the fixing member. Hence, along with inflation of the fluid bag, if the fixing member applies a force to tighten the wrist, since the gap is formed between the wrist surface at which the non-selected artery is located and the fixing member, oppression of the non-selected artery can be avoided. Further, along with inflation of the fluid bag, the wrist surface at which the non-selected artery is located and the fixing member contact with each other, and if the gap is eliminated, the oppressing pressure is small because the gap was initially present, and inconvenience by oppression of the non-selected artery can be avoided.

In the wrist type blood pressure meter cuff, preferably, the fixing member includes a swollen part of at least part of inner surface of the position coinciding with the non-selected artery swollen in the outward direction. In such configuration, a gap can be formed between at least part of the wrist surface at which the non-selected artery is located and the fixing member.

In the wrist type blood pressure meter cuff, preferably, the fixing member includes a spacer abutting against the wrist, and the gap is formed by this spacer. In this configuration, a gap can be formed between at least part of the wrist surface at which the non-selected artery is located and the fixing member. Further, the inner surface of the spacer may be formed along the bone of the wrist. In this case, the gap is maintained securely, and the cuff can be stably fixed at the wrist.

In the wrist type blood pressure meter cuff, preferably, the fixing member has a structure so that the rate of area of direct contact of the fixing member at the wrist at which the non-selected artery is located is smaller than the rate of area of direct contact of the fixing member in other position of the wrist. In such configuration, the oppressing surface of the non-selected artery is smaller than other part, and oppressing pressure on the non-selected artery can be decreased.

In the wrist type blood pressure meter cuff, preferably, the fixing member has an opening in the position coinciding with the non-selected artery. In this configuration, the area of the fixing member directly contacting with the wrist surface at which the non-selected artery is located is decreased.

In the wrist type blood pressure meter cuff, preferably, the fixing member includes a discontinuous part in the position coinciding with the non-selected artery of the fixing member to compose a fixing member main body, and the discontinuous part is coupled by a coupling member of which width in the longitudinal direction of artery is narrower than the fixing member main body. In this configuration, the rate of the area of the fixing member directly contacting with the wrist surface at which the non-selected artery is located is smaller.

DESCRIPTION OF THE PREFERRED EMBODIMENTS

Preferred embodiments of wrist type blood pressure meter cuff are described below while referring to the drawings.
(Embodiment 1)

Figure 1:
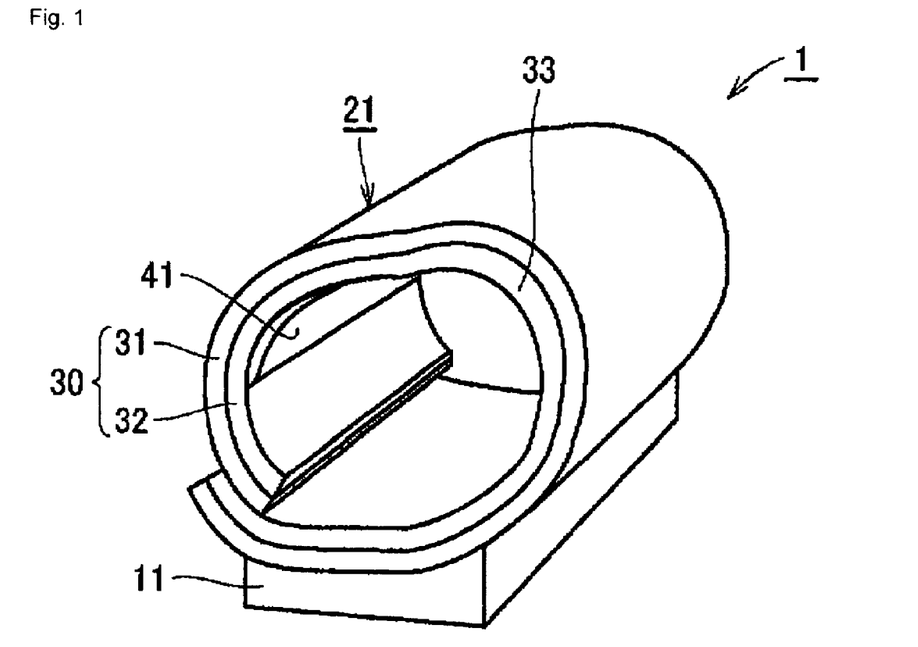
FIG. 1 shows a perspective view of a structure of a wrist type blood pressure meter in a first embodiment of the invention.
Figure 2:
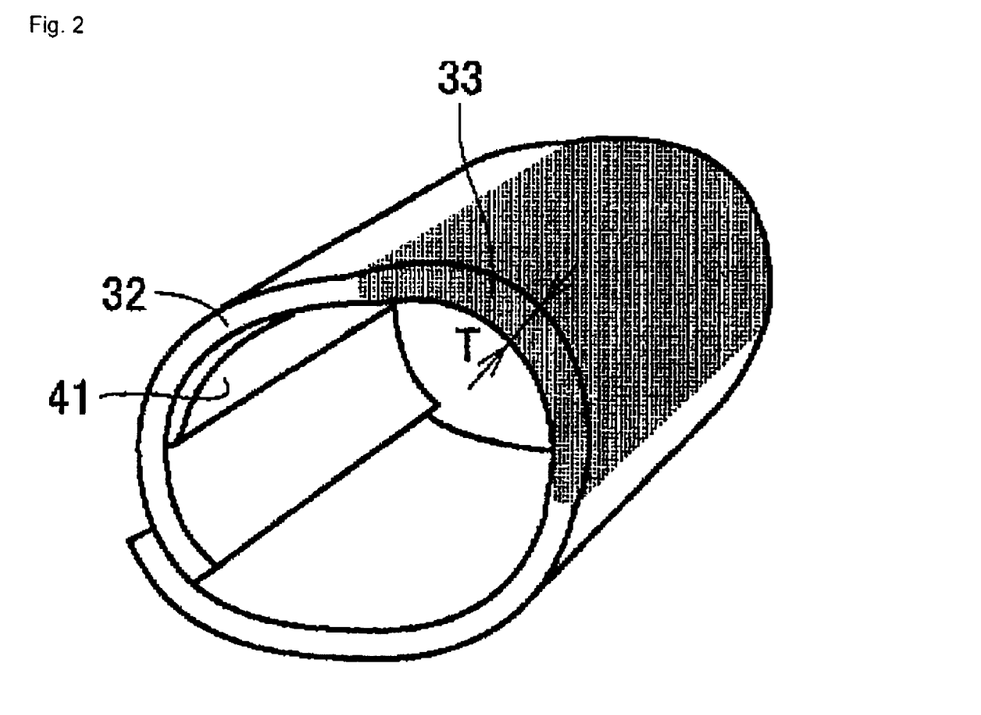
FIG. 2 shows a perspective view of a structure of a curler of fixing member of the wrist type blood pressure meter cuff in the first embodiment of the invention.

A wrist type blood pressure meter cuff in this embodiment is explained by referring to FIG. 1 to FIG. 3. FIG. 1 is a perspective view showing a structure of a wrist type blood pressure meter in this embodiment, FIG. 2 is a perspective view showing a structure of a curler of fixing member of a wrist type blood pressure meter cuff in the embodiment, and FIG. 3 is a sectional view explaining the state of use of the wrist type blood pressure meter cuff in the embodiment.
(Structure of Wrist Type Blood Pressure Meter Cuff)

A structure of a wrist type blood pressure meter cuff is explained. As shown in FIG. 1, a wrist type blood pressure meter cuff 21 is integrated with a blood pressure meter main body 11, and a blood pressure meter 1 is composed. The cuff 21 is composed of fixing member 30 including a band 31 and a curler 32, and a fluid bag 41 fixed to its inner surface. The blood pressure meter main body 11 incorporates a pump for feeding air into the fluid bag 41, and also comprises a sensor for detecting the pressure of the fluid bag 41, and a control device for controlling their actions.

The blood pressure meter 1 of the embodiment is designed to measure blood pressures by selecting one artery out of two arteries running in the wrist, and oppressing only the selected artery. The wrist 65 includes, as mentioned above, the radial artery 62 running along the radius 61 and the ulnar artery 64 running along the ulna 63, and only one of them is selectively oppressed for measuring blood pressures. During measurement of blood pressures, the fluid bag 41 is inflated to oppress the wrist 65, and the structure is designed so that the oppressing pressure directly applied from the fixing member 30 to the wrist 65 at which the non-selected artery is located may be smaller than the oppressing pressure applied directly from the fixing member 30 to other position of the wrist 65.

The band 31 is made of a hardly stretchable cloth or the like, and a flat fastener for fixing the end portion adjustably in position is fitted to its end portion. The curler 32 fixed to the inner surface side of the band 31 by adhesive or the like is made of synthetic resin material such as polypropylene which is stiffer than the cloth and is slightly deformed at the time of mounting.

As shown in FIG. 2, the curler 32 is made of a rectangular plate formed in a slightly round shape nearly along the wrist surface. A part of the curler 32 has a thick swollen part 33 of which inner surface is slightly swollen to outside than other part along the axial direction. The thickness of the swollen part 33 is about 2.6 mm in this embodiment, and other part is about 1.3 mm. The swollen part 33 is thick because it is reinforced so as not to be deformed easily, and it is desired to have a thickness of about two times that of other part.

The inner surface of the swollen part 33 is also swollen to outside, and this swollen part 33 is, as shown in FIG. 3, fixed to the wrist 65 so as to be coinciding with the non-selected artery 64. By the swollen part 33, a gap S is formed between the surface of the wrist and the inner surface of the swollen part 33 swollen to outside. The gap S is formed in the overall length of the fixing member 30 coinciding with the non-selected artery 64. At this time, it is desired that the end portion of the swollen part 33 may contact with the bone 63 of the wrist 65. The swollen part 33 straddles over the non-selected artery 64 as shown in FIG. 3, and one end contacts with the middle between the selected artery 62 to be measured and the non-selected artery 64, and other end contacts with the bone 63 along the non-selected artery 64 by way of the skin.

The fluid bag 41 is composed of an elastic material such as thin film silicone rubber or latex film, and is formed in a rectangular shape in plane view in the overall length in the axial direction of the curler 32. The fluid bag 41 is a bag, and it is filled with air and inflated.
(Use Method of Wrist Type Blood Pressure Meter Cuff)

The use method of the cuff of the embodiment is explained by referring to FIG. 3. In FIG. 3, the blood pressure meter main body is not shown.

Figure 3A:
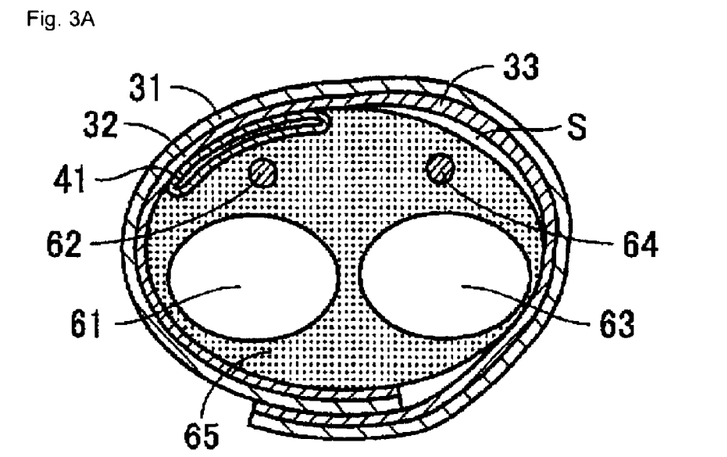
FIG. 3 shows a sectional view explaining the state of use of the wrist type blood pressure meter cuff in the first embodiment of the invention.

The cuff 21 is extended and wound around the wrist 65, and both end portions are fixed by a flat fastener. At this time, the fluid bag 41 is adjusted to contact with the surface of the wrist 65 at the location of the artery 62 selected for measurement (FIG. 3A). In this embodiment, it is explained that the radial artery 62 is selected as the object of measurement.

When the fluid bag 41 contacts with the surface side of the radial artery 62, the swollen part 33 of the curler 32 contacts with the surface side of the ulnar artery 64 as the non-selected artery. This swollen part 33 produces a gap S against the wrist 65 in a contracted state of the fluid bag 41. The swollen part 33 straddles over the ulnar artery 64, and one end is positioned nearly in the middle of the radial artery 62 to be measured and the non-selected ulnar artery 64, and other end is positioned at the surface side of the ulna 63 along the non-selected ulnar artery 64.

Figure 3B:
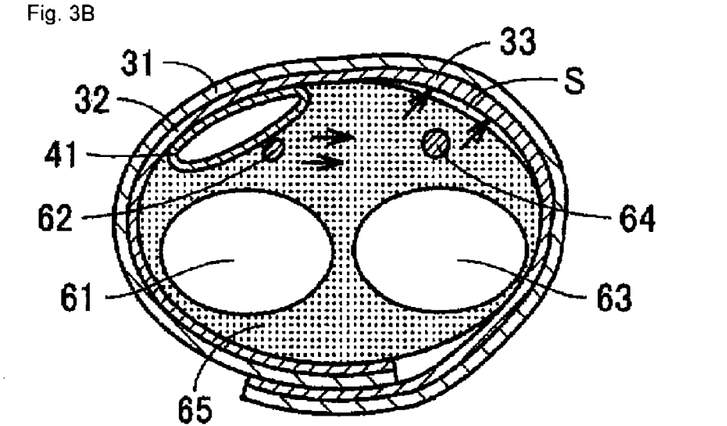

In this state, as the fluid bag 41 is inflated with air, as shown in FIG. 3B, the radial artery 62 to be measured is oppressed. At the same time, the fixing member 30 applies a force to tighten the entire wrist 65. At this time, in this embodiment, since a gap S is formed between the surface of the wrist 65 at the location of the non-selected ulnar artery 64 and the inner surface of the fixing member 30, direct oppressing pressure is not generated on the surface of the wrist 65 at the location of the ulnar artery 64 from the fixing member 30. At the same time, the oppressing pressure applied from the fluid bag 41 in the direction of the ulnar artery 64 through the human body of the wrist 65 is lessened as the wrist 65 is swollen in the direction of the gap S.

The swollen part 33 has a double thickness as compared with other parts, and is less likely to be deformed than other parts. Accordingly, if the tightening force on the curler 32 is applied by the band 31 as the fluid bag 41 is inflated, the swollen part 33 is hardly deformed, and this gaps can be maintained. Moreover, since one end of the swollen part 33 contacts with the surface side of the ulna 63, biting of one end of the swollen part 33 into the wrist can be prevented, and the effect of maintaining the gap S is greater.

Figure 3C:
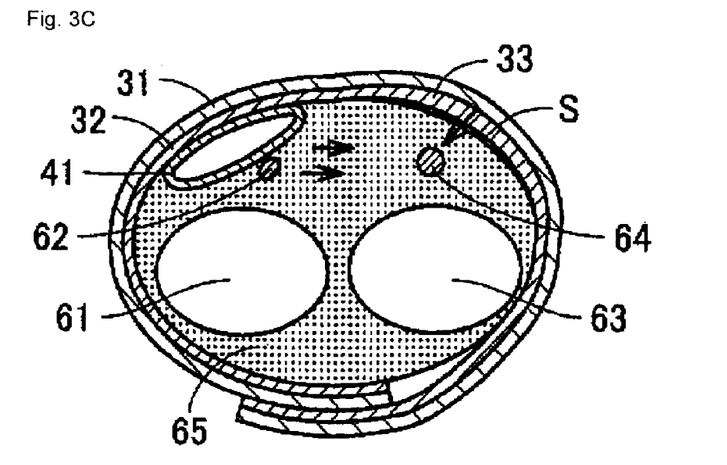

If the wrist is brought into contact with the inner surface of the curler 32 as shown in FIG. 3C, since the gap S was formed initially, the oppressing pressure applied to the ulnar artery 64 can be alleviated.

(Action and Effect)

As described herein, according to the wrist type blood pressure meter cuff of the embodiment, oppressing pressure applied to the non-selected artery 64 can be decreased. Hence, pulse waves of the selected artery 62 are detected by the sensor connected to the fluid bag 41 for oppressing it, but pulse waves of non-selected artery 64 are hardly transmitted to the fluid bag 41. As a result, when detecting the pulsations of the selected artery 62 by the sensor through the fluid bag 41, pulse waves of the non-selected artery 64 are prevented from mixing into the pulse waves of the selected artery 62 necessary for measurement of blood pressures, thereby avoiding disturbance of measurement of blood pressures.

In this embodiment, by increasing the thickness of the swollen part 33 of the curler 32, it is less likely to be deformed than other parts, by changing the material of the swollen part 33 only, it is made less likely to be deformed, and the shape of the gap S may be maintained. As the material, titanium or other hard metal material may be used.

If the swollen part 33 is formed in the same material and same thickness as other parts, by forming the curler 32 by a proper hard material, deformation of the gap S formed by the swollen part 33 maybe avoided to a certain extent, and oppressing pressure on the non-selected artery can be lessened.

In this embodiment, the swollen part 33 is formed in the overall length in the axial direction of the fixing member 30, but the swollen part 33 may be formed only in part of the overall length of the fixing member 30. As mentioned above, the wrist 65 includes the radius 61 along the radial artery 62 and the ulna 63 along the ulnar artery 64. The radius 61 and ulna 63 have protrusions called styloid process of radius and styloid process of ulna respectively at the wrist, and in these areas the radial artery 62 and ulnar artery 64 are positioned closer to the skin and are likely to be oppressed. When it is designed not to oppress the position around the skin of such non-selected artery, pulsations generated from the non-selected artery can be considerably suppressed. Accordingly, the swollen part 33 may be formed so as to swell only the portions corresponding to the styloid process of radius and styloid process of ulna to the outside.

In this embodiment, the fixing member 30 is composed of band 31 and curler 32, but the fixing member 30 may be composed by integrally forming them. In the following embodiments 2 to 4, the fixing member 30 integrally forming the band 31 and curler 32 is shown.

(Embodiment 2)

Figure 4:
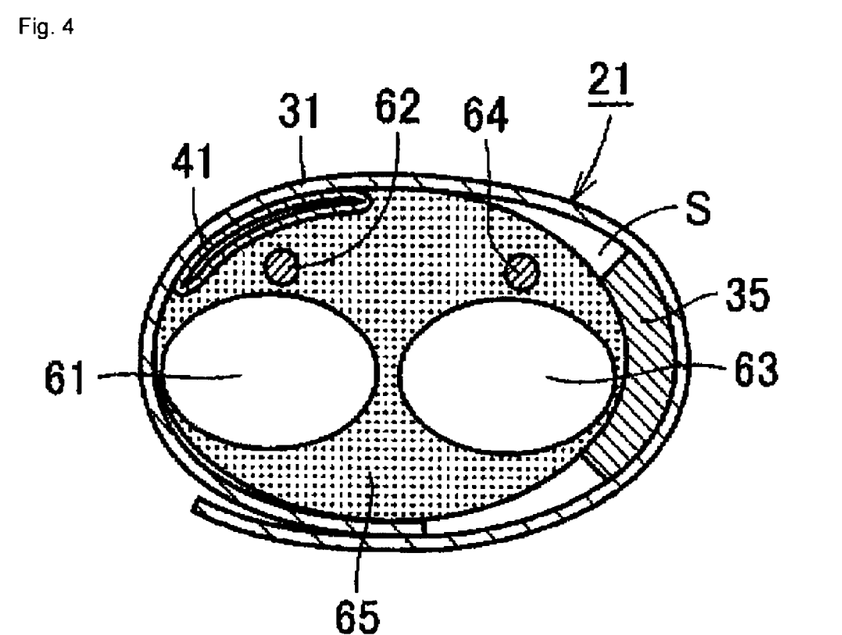
FIG. 4 shows a sectional view explaining the state of use of a wrist type blood pressure meter cuff in a second embodiment of the invention.

A wrist type blood pressure meter cuff in this embodiment is explained by referring to FIG. 4, and only the structure different from the foregoing embodiment is described. FIG. 4 is a sectional view explaining the state of use of the wrist type blood pressure meter cuff in this embodiment.

As shown in FIG. 4, in this embodiment, by a spacer 35 provided at the inner surface side of a fixing member 30, a gap S is formed between the non-selected artery 64 and the fixing member 30. The spacer 35 is composed of an elastic material such as foamed urethane, and its inner surface is formed in a C-figure along the bone 63 of the wrist 65. In this configuration, when the cuff 21 is worn, as shown in FIG. 4, the spacer 35 is properly deformed, and its inner side fits to the bone 63 of the wrist 65; and the cuff 21 can be stably fixed. At the same time, the gap S can be formed securely.

When the fluid bag 41 is inflated with air and the fluid bag 41 is expanded until the fixing member 30 applies a force to tighten the entire wrist 65, since the gap S can be held by the spacer 35, direct oppression of the non-selected artery 64 by the fixing member 30 can be avoided.

(Embodiment 3)

Figure 5:
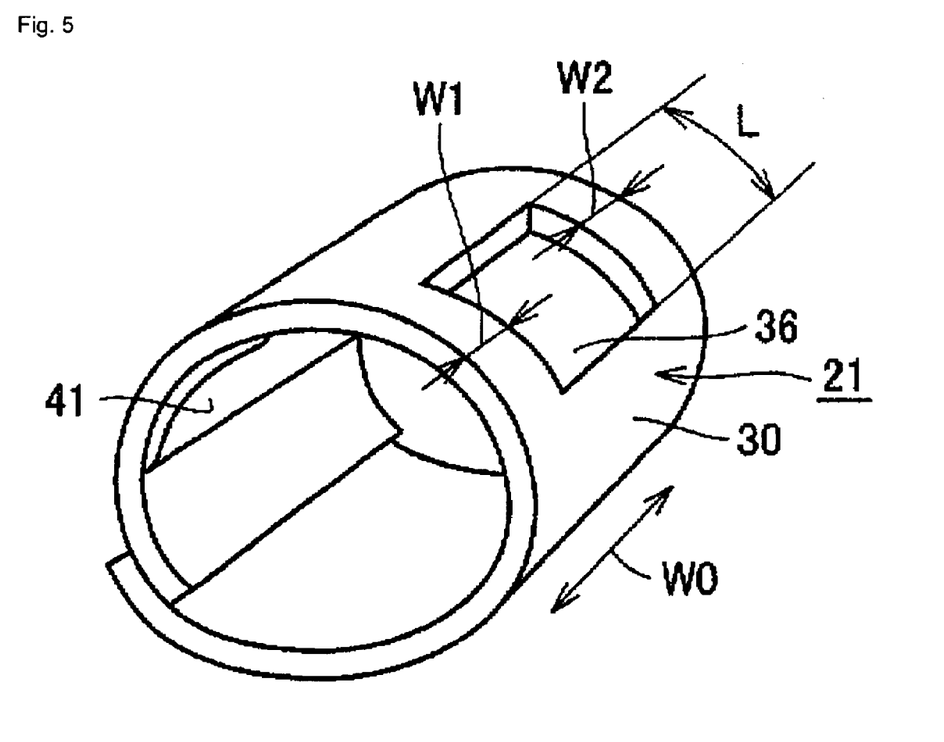
FIG. 5 shows a perspective view of a wrist type blood pressure meter cuff in a third embodiment of the invention.

A wrist type blood pressure meter cuff in this embodiment is explained by referring to FIG. 5 and FIG. 6, and only the structure different from embodiment 1 is described. FIG. 5 is a perspective view of the wrist type blood pressure meter cuff in the embodiment, and FIG. 6 is a sectional view explaining the state of use of the wrist type blood pressure meter cuff in this embodiment.

In this embodiment, a fixing device 30 has an opening 36, and the rate of area of direct contact of the fixing member 30 at the wrist 65 at which the non-selected artery is located is set smaller than the rate of area of direct contact of the fixing member 30 in other position of the wrist 65. That is, at the wrist 65 of the location of the non-selected artery, since the opening 36 is formed in the fixing member 30, the fixing member 30 contacts directly only in the area other than the opening 36, and the rate of area of direct contact of the fixing member 30 is smaller than in other part of direct contact in the entire surface of the fixing member 30.

The opening 36 is provided in the portion coinciding with the non-selected artery 64 of the fixing member 30. The opening 36 acts as a relief for releasing the oppressing pressure applied to the non-selected artery, and it is desired to be as large as possible. However, necessary strength is required as the fixing member, and the total of width W1 and W2 in the positions at both sides of the opening 36 should be set at ⅛ or more to ¼ or less of the width W0 the fixing member 30 in the axial direction of the wrist. For example, when the width W0 is 40 mm, W1 and w2 are respectively 2.5 mm or more to 5 mm or less.

The length L of the wrist 65 in the peripheral direction is also desired to be as long as possible, but considering the required strength of the fixing member 30, the length L should be 20 mm or more. When the length is 20 mm, an opening of 10 mm is formed respectively at both sides of the non-selected artery, and a sufficient effect is obtained in the case of the wrist 65 of a standard size.

Figure 6A:
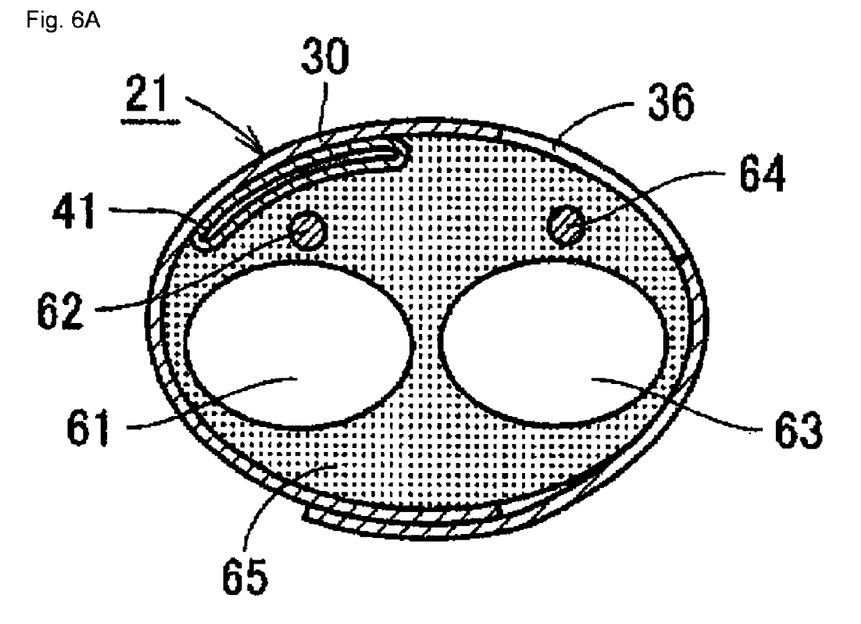
FIG. 6 shows a sectional view explaining the state of use of the wrist type blood pressure meter cuff in the third embodiment of the invention.
Figure 6B:
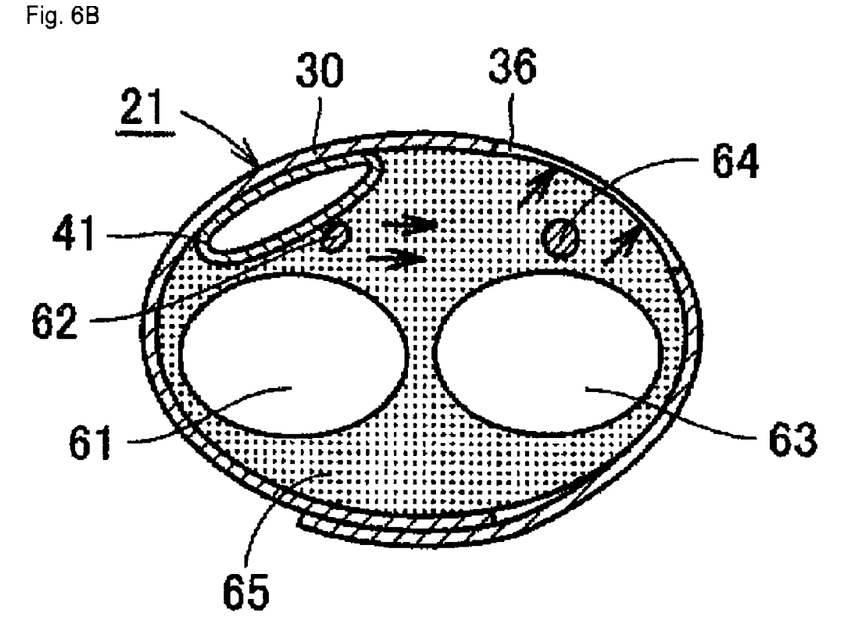

FIG. 6A shows a contracted state of the fluid bag 41. In this state, neither the radial artery 62 to be measured nor the non-selected ulnar artery 64 is oppressed at all. As shown in FIG. 6B, when the fluid bag 41 is expanded by inflating the fluid bag 41 with air, oppressing pressure is applied to the radial artery 62. At the same time, the fixing device 30 produces a force for tightening the wrist 65, but since the opening 36 is formed at the surface side of the ulnar artery 64, oppressing pressure is not directly applied from the fixing member 30 in this area. Further, as the wrist 65 is swollen to this direction, the pressure acting on the ulnar artery 64 from the fluid bag 41 through the human body can be lessened.

In this embodiment, a rectangular opening is formed, but the shape is not specified. When the fixing member 30 is composed in a double structure of band and curler, as far as the curler has a certain thickness, an opening may be formed only in the curler, and opening is not needed in the band for covering it, and the same effects are obtained.

(Embodiment 4)

Figure 7:
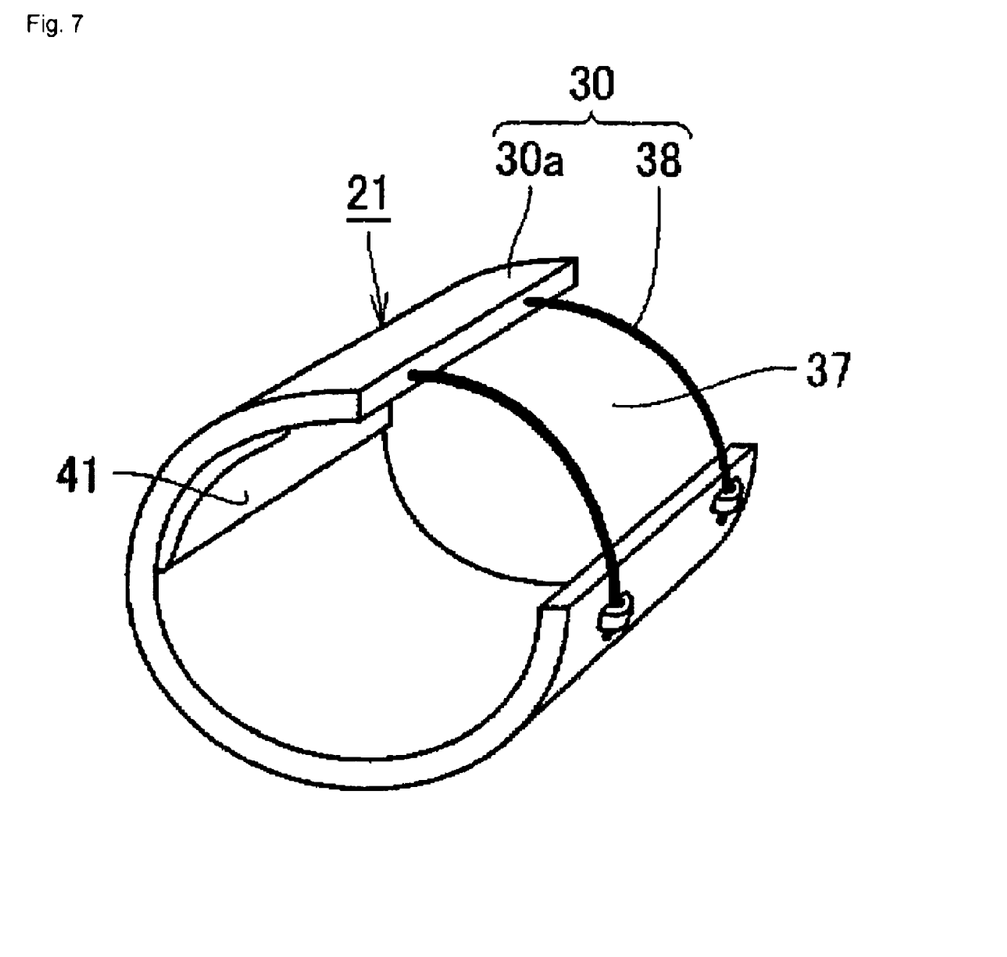
FIG. 7 shows a perspective view of a wrist type blood pressure meter cuff in a fourth embodiment of the invention.

A wrist type blood pressure meter cuff in this embodiment is explained by referring to FIG. 7 and FIG. 8, and only the structure different from embodiment 3 is described. FIG. 7 is a perspective view of the wrist type blood pressure meter cuff in the embodiment, and FIG. 8 is a sectional view explaining the state of use of the wrist type blood pressure meter cuff in this embodiment.

In this embodiment, a fixing device 30 has a discontinuous part 37 in a portion coinciding with the non-selected artery, and a fixing member main body 30a is composed, and the discontinuous part 37 is composed by coupling with a coupling member 38 of which width in the longitudinal direction of the artery is narrower than the fixing member main body 30a.

The coupling member 38 is composed of metal wire or the like, and one end of the coupling member 38 is fixed tot he end portion opposite to the discontinuous part 37 of the fixing member main body 30a, and other end is adjustably fixed to the end of the opposite side of the fixing member main body 30a. The coupling member 38 may be made of any less stretchable material, including any material other than metal. It may be formed like a belt.

Figure 8A:
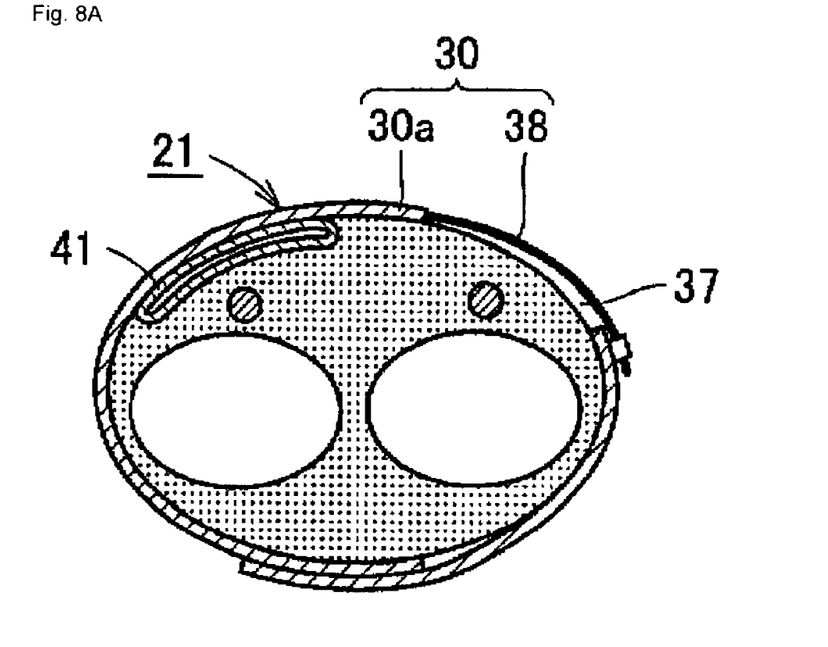
FIG. 8 shows sectional view explaining the state of use of the wrist type blood pressure meter cuff in the fourth embodiment of the invention.
Figure 8B:
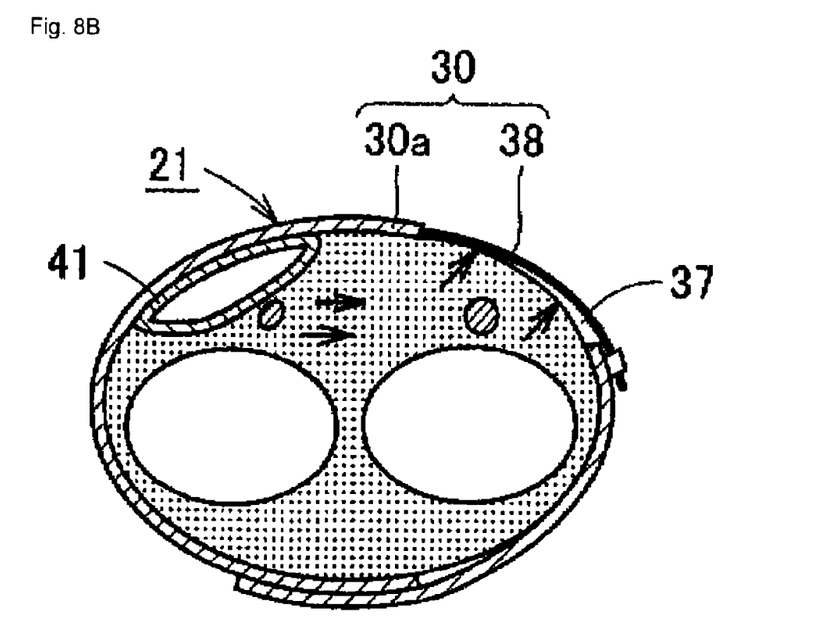

When using the cuff 21 of this embodiment, from a contracted state of the fluid bag 41 as shown in FIG. 8A, the fluid bag 41 is expanded as shown in FIG. 8B, and if the fixing member 30 produces a force to tighten the wrist 65, oppressing pressure is not applied in the portion excluding the existing area of the coupling member 38 of the discontinuous part 37. If oppressing pressure of the fluid bag 41 is applied to the wrist 65 through the human body, since the wrist 65 is swollen to the discontinuous part 37, and its oppressing pressure can be lessened.

In this embodiment, since the covering part of the non-selected artery 64 is composed of the coupling member 38, oppressing pressure to the non-selected artery 64 is free from effects of the material and shape of the fixing member main body 30a. Therefore, the material and shape of the fixing member main body 30a can be selected freely.

The foregoing embodiments are only presented as examples, and are therefore illustrative and not restrictive. Therefore the scope of the invention is defined by the appended claims rather than by the description preceding them, and all changes that fall within metes and bounds of the claims, or equivalence of such metes and bounds thereof are therefore intended to be embraced by the claims.

According to the wrist type blood pressure meter cuff of the invention, oppressing pressure to the non-selected artery can be lessened, and pulse waves of the non-selected artery are prevented from mixing into pulse waves of the selected artery necessary for measurement of blood pressures, so that disturbance in measurement of blood pressures can be avoided.

What is claimed is:

1. A wrist type blood pressure meter cuff comprising a fluid bag for compressing a selected artery of a radial artery or ulnar artery located at a wrist of a user by feeding fluid to the fluid bag to inflate the fluid bag, and a fixing member for fixing the fluid bag at the wrist, wherein the fixing member has a structure so that the compressing pressure directly applied from the fixing member to the wrist at which the non-selected artery is located may be smaller than the compressing pressure directly applied from the fixing member to another position of the wrist when compressing the wrist by inflating the fluid bags, wherein the fixing member has a shape so as to form a gap between the surface of the wrist at the location of the non-selected artery and a surface of the inner surface of the fixing member, when the wrist type blood pressure meter cuff is fixed at the wrist in a contracted state of the fluid bag and wherein the fixing member includes a swollen part of at least part of inner surface of the position coinciding with the non-selected artery swollen in the outward direction.

2. The wrist type blood pressure meter cuff according to claim 1, wherein the fixing member has a structure so that the rate of area of direct contact of the fixing member at the wrist at which the non-selected artery is located is smaller than the rate of area of direct contact of the fixing member in another position of the wrist.

3. The wrist type blood pressure meter cuff according to claim 2, wherein the fixing member has an opening in the position coinciding with the non-selected artery.

4. The wrist type blood pressure meter cuff according to claim 2, wherein the fixing member includes a discontinuous part in the portion of the fixing member coinciding with the location of the non-selected artery such that the continuous portion of the fixing member comprises a fixing member main body, and the discontinuous part is coupled by a coupling member having a width in the longitudinal direction of the non-selected artery is narrower than that of the fixing member main body.

5. A wrist type blood pressure meter cuff comprising a fluid bag for compressing a selected artery of a radial artery or ulnar artery located at a wrist of a user by feeding fluid to the fluid bag to inflate the fluid bag, and a fixing member for fixing the fluid bag at the wrist.

wherein the fixing member has a structure so that the compressing pressure directly applied from the fixing member to the wrist at which the non-selected artery is located may be smaller than the compressing pressure directly applied from the fixing member to other position of the wrist when compressing the wrist by inflating the fluid bag, wherein the fixing member has a shape so as to form a gap between the surface of the wrist at the location of the non-selected artery and a surface of the inner surface of the fixing member, when the wrist type blood pressure meter cuff is fixed at the wrist in a contracted state of the fluid bag and wherein the fixing member includes a spacer adapted to abut against the wrist, and the gap is formed by this spacer.

6. The wrist type blood pressure meter cuff according to claim 5, wherein the spacer has a shape of which an inner surface is adapted to curved along the bone of the wrist.

* * * * *